(12) United States Patent
Jung et al.

(10) Patent No.: US 8,093,350 B2
(45) Date of Patent: Jan. 10, 2012

(54) COORDINATION POLYMER CRYSTAL WITH POROUS METAL-ORGANIC FRAMEWORKS AND PREPARATION METHOD THEREOF

(75) Inventors: Dong-Hyun Jung, Suwon-si (KR); Min-Kyoung Kim, Yongin-si (KR); Dae-Jin Kim, Seoul (KR); Tae-Bum Lee, Seoul (KR); Seung-Hoon Choi, Suwon-si (KR); Ji-Hye Yoon, Geoje-si (KR); Sang-Beom Choi, Daejeon (KR); You-Jin Oh, Bucheon-si (KR); Min-Jeong Seo, Seoul (KR); Ja-Heon Kim, Gwangju-si (KR); Byoung-Ho Won, Seoul (KR); Ki-Hang Choi, Seoul (KR)

(73) Assignee: Insilicotech Co., Ltd, Seongnam-Si (KR)

( * ) Notice: Subject to any disclaimer, the term of this patent is extended or adjusted under 35 U.S.C. 154(b) by 567 days.

(21) Appl. No.: 12/294,631

(22) PCT Filed: Nov. 30, 2007

(86) PCT No.: PCT/KR2007/006166
§ 371 (c)(1),
(2), (4) Date: Sep. 26, 2008

(87) PCT Pub. No.: WO2008/082087
PCT Pub. Date: Jul. 10, 2008

(65) Prior Publication Data
US 2010/0174047 A1    Jul. 8, 2010

(30) Foreign Application Priority Data

Jan. 3, 2007    (KR) ........................ 10-2007-0000570

(51) Int. Cl.
*C08G 79/00* (2006.01)
*C08G 79/14* (2006.01)
*C08F 6/06* (2006.01)
*C08J 3/11* (2006.01)
(52) U.S. Cl. ......... 528/395; 528/490; 528/492; 528/503
(58) Field of Classification Search .................. 528/395, 528/490, 492, 503
See application file for complete search history.

(56) References Cited

FOREIGN PATENT DOCUMENTS

| KR | 10-2005-0099239 A | 10/2005 |
|----|-------------------|---------|
| WO | 02/088148 A1 | 11/2002 |
| WO | 2003-064030 A1 | 8/2003 |
| WO | 2003-102000 A1 | 12/2003 |
| WO | 2004-101575 A2 | 11/2004 |
| WO | 2005-049484 A1 | 6/2005 |
| WO | 2006-028479 A1 | 3/2006 |
| WO | 2006-050898 A1 | 5/2006 |

OTHER PUBLICATIONS

Rosi, N.L., et al., "Hydrogen Storage in Microporous Metal-Organic Frameworks," Science, vol. 300, May 16, 2003, pp. 1127-1129.

(Continued)

*Primary Examiner* — Duc Truong
(74) *Attorney, Agent, or Firm* — Sughrue Mion, PLLC (57) ABSTRACT

Disclosed is a coordination polymer crystal with porous metal-organic frameworks (MOFs), in which, while a crystal state of the coordination polymer crystal is maintained, an additional material selected from the group consisting of an organic compound, a metal cluster, and an organometallic compound is chemically bonded to the coordination polymer crystal. Therefore it is possible easily adsorb and store more guest molecules regardless of a change in an ambient temperature or pressure due to the chemically bonded additional material.

20 Claims, 6 Drawing Sheets

OTHER PUBLICATIONS

Zhao, X., et al., "Hysteretic Adsorption and Desorption of Hydrogen by Nanoporous Metal-Organic Frameworks," Science, vol. 306, 2004, pp. 1012.

European Patent Office, European Search Report issued in corresponding EP Application No. 07851169.8, dated Mar. 10, 2011.

Seo et al., "A Homochiral Metal-Organic Porous Material for Enantioselective Separation and Catalysis," Nature, 2000, vol. 404, pp. 982-986.

COORDINATION POLYMER CRYSTAL WITH POROUS METAL-ORGANIC FRAMEWORKS AND PREPARATION METHOD THEREOF

This is a national stage application under 35 U.S.C. §371 of PCT/KR2007/006166 filed on Nov. 30, 2007, which claims priority to Korean patent application 10-2007-0000570 filed on Jan. 3, 2007, all of which are incorporated herein by reference.

TECHNICAL FIELD

The present invention relates to a coordination polymer crystal with porous metal-organic frameworks, which can adsorb/desorb gas or organic molecules, and a method of preparing the same.

BACKGROUND ART

Recently, many countries have tried to develop wind power, tidal power, geothermal energy, solar energy, hydrogen gas, etc. as energy sources for replacing depletable fossil fuels. Especially, from among such energy sources, hydrogen gas has the highest energy efficiency per unit mass and no harmful byproducts of combustion, and thus research on the preparation, storage, transportation, etc. thereof has been conducted. In particular, a focus is placed on research on the practical use of a fuel cell and the development of a material for efficiently storing hydrogen gas.

Currently, materials capable of storing hydrogen gas include metal hydride, carbon nanotube, carbon compound such as activated carbon, zeolite, metal-organic framework (MOF), etc. Especially, the MOF has been noticed due to a higher specific surface area than those of other materials, and accordingly, the possibility of reversibly storing hydrogen.

Figure 1:
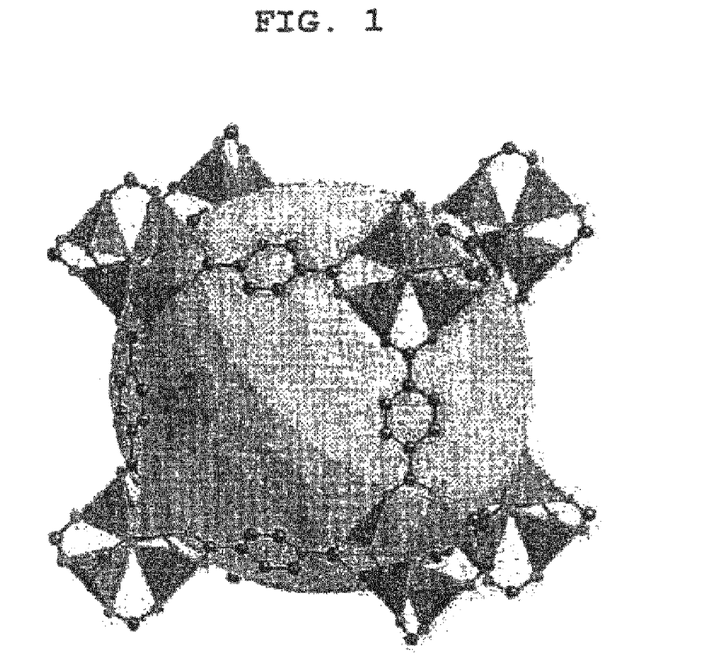
FIG. 1 is a three-dimensional structural view illustrating a lattice cell of MOF-5 [Zn$_4$(O)O$_{12}$C$_6$] in a conventional coordination polymer crystal with porous metal-organic frameworks (MOFs)

The MOF is a kind of organic-inorganic hybrid compound, in which a metal and an organic ligand are three-dimensionally linked via the organic ligand functioning as a linker. Specifically, as shown in FIG. 1, the MOF refers to a material in which the organic ligand is coordinated to at least two metals, and each of the coordinated metals is coordinated in a chain-like manner to at least one other organic ligand, thereby forming many tiny spaces, i.e. a network structure with pores, inside the framework.

Such a MOF is prepared by various preparation methods. For example, the MOF can be prepared through a substitution reaction of organic ligand ions by using metal salts as a metal source. Specifically, in such preparation, zinc nitrate [Zn(NO$_3$)$_2$] as the metal source, and a dicarboxylic acid-based compound as the ligand are mainly used so as to prepare the framework (O. M. Yaghi et al. Science, 2003, vol. 300, p. 1127; WO 02/088148).

Also, an isoreticular metal-organic framework (IRMOF) can be prepared by using zinc as the metal source to thereby form core zinc oxide (Zn$_4$O) and by using an organic ligand such as a dicarboxylic group. In addition, metal ions such as Cu and Fe (instead of zinc) as a core, and a tridentate or multidentate organic ligand can be used to prepare a MOF.

As described above, in a prior art, various organic ligands and metals have been used to prepare MOFs having various structures in such a manner that a MOF can store as much hydrogen as possible. However, it has been known that such a conventional MOF cannot store a large amount of hydrogen gas at an ambient temperature and an atmospheric pressure, so the storage capacity of the hydrogen gas does not reach a required level. In other words, in the conventional MOF, hydrogen gas is adsorbed to only some spaces, from among the whole spaces for adsorbing hydrogen gas, and most of the spaces remain empty. Thus, the storage of hydrogen gas is not efficient.

In addition, when an ambient pressure or temperature changes, the conventional MOF reversibly physically adsorbing hydrogen gas can not keep its stable storage of the hydrogen gas. Accordingly, in storing and/or transporting the hydrogen gas by using the MOF, expensive equipment has been required to maintain a fixed temperature or pressure. Therefore, Matthew J. Rosseinsky et al. provided Ni$_2$(bipy)$_3$(NO$_3$)$_4$, that is, a MOF which can irreversibly physically adsorb hydrogen, in "Hysteretic Adsorption and Desorption of Hydrogen by Nanoporous Metal-Organic Frameworks"(Science, Vol. 306, p. 1012). However, this MOF has a two-dimensional structure (like a structure of graphite), not a three-dimensional structure, and thus is less suitable for a material for storing hydrogen due to instability in the structure (for example, the structure may be easily broken).

DISCLOSURE OF THE INVENTION

As described above, when a coordination polymer crystal with porous metal-organic frameworks (MOFs) physically adsorbs and stores a guest molecule, it is not easy to adsorb the guest molecule because a pore size within the crystal is larger than the size of the guest molecule (e.g., hydrogen gas, etc.). In addition, since the storage state of the guest molecule is sensitive to changes in an ambient temperature or pressure, the efficiency of storing the guest molecule is decreased.

Accordingly, the present invention has been made to solve the above-mentioned problems. We have found that while a coordination polymer crystal with porous MOFs is maintained, an additional material such an organic compound, a metal cluster, or an organometallic compound is chemically bonded to the coordination polymer crystal, and thus, it is possible to adjust the pore size, and at the same time to prevent the stored guest molecules from releasing according to a change in an ambient temperature or pressure.

It is an object of the present invention to provide a coordination polymer crystal which can continuously store more guest molecules, and a method of the same.

According to an aspect of the present invention, there is provided a coordination polymer crystal with porous metal-organic frameworks (MOFs), in which, while a crystal state of the coordination polymer crystal is maintained, an additional material selected from the group including an organic compound, a metal cluster, and an organometallic compound is chemically bonded to the coordination polymer crystal.

In accordance with another aspect of the present invention, there is provided a method of preparing a coordination polymer crystal, the method including the steps of: (i) preparing a coordination polymer crystal with porous metal-organic frameworks (MOFs); and (ii) chemically bonding at least one additional material selected from the group consisting of an organic compound, a metal cluster, and an organometallic compound, to the coordination polymer crystal.

BRIEF DESCRIPTION OF THE DRAWINGS

The foregoing and other objects, features and advantages of the present invention will become more apparent from the following detailed description when taken in conjunction with the accompanying drawings in which.

BEST MODE FOR CARRYING OUT THE INVENTION

Reference will now be made in detail to the exemplary embodiments of the present invention.

A coordination polymer crystal with porous metal-organic frameworks (MOFs) according to the present invention refers to a crystalline compound in which a metal is coordinated to an organic ligand so as to form one-, two-, and three dimensional porous structures as shown in FIG. 1. Such a coordination polymer crystal stably maintains a pore structure, even when a solvent or a guest molecule is adsorbed to or desorbed from the inside of the pore, and thus is useful to store gas such as hydrogen gas. In general, a coordination polymer crystal having such porous MOFs is prepared by a reaction of a metal precursor with an organic molecule within a solvent.

The present invention is characterized by chemically bonding an additional material such as an organic compound, a metal cluster, or an organometallic compound, to a coordination polymer crystal with porous MOFs.

Usually, a coordination polymer crystal with porous MOFs physically adsorbs hydrogen gas. In the physical adsorption, adsorbed material is adsorbed onto adsorbing material by van der Waals force, which acts in a short distance. Accordingly, the distance of the adsorbed material from the adsorbing material is required to be within a range which van der Waals force can act. However, as known to those skilled in the art, a coordination polymer crystal with porous MOFs has a pore size (average particle diameter) larger than a hydrogen molecule diameter (about 2.89 Å). Then, generally, it is difficult for a distance of hydrogen gas from a pore surface of the coordination polymer crystal to be within a range which van der Waals force can act. Therefore, the hydrogen gas cannot be easily adsorbed to the coordination polymer crystal. In other words, the coordination polymer crystal adsorbs and stores hydrogen gas in only some parts of the organic ligand and/or the metal which can adsorb hydrogen gas, thereby reducing the efficiency of the adsorption. In order to solve this problem, conventionally, more hydrogen gas has been compressed at a higher pressure or at a lower temperature, and has been stored in the coordination polymer crystal.

Also, in physical adsorption, contrary to chemical adsorption, adsorbed material is adsorbed onto adsorbing material by van der Waals force without a change in a molecular structure, or electron transfer between the adsorbed material and the adsorbing material. Herein, a distance between adsorbed material and adsorbing material, rather than type or property of the adsorbed material, is influential. Usually, molecular motion is more active at a high temperature or at a low pressure, and herein, a distance between molecules changes according to a change in a temperature or a pressure. In other words, when an ambient temperature or pressure is changed, a distance between adsorbed material and adsorbing material is also changed. Accordingly, according to a change in an ambient temperature or pressure, hydrogen gas can be adsorbed to the coordination polymer crystal with porous MOFs, and the adsorbed hydrogen gas can be desorbed from the coordination polymer crystal. Therefore, in storing and transporting hydrogen gas by using a conventional coordination polymer crystal, expensive equipment has been required to maintain a fixed ambient temperature or pressure.

In the present invention, in order to sufficiently utilize the whole of pore spaces within the coordination polymer crystal with porous MOFs as effective spaces for adsorption of guest molecules, an additional material (such as an organic compound, a metal cluster, or an organometallic compound) is chemically bonded to the coordination polymer crystal, thereby increasing the storage, capacity of guest molecules. The additional material is used to adjust a pore size, to increase an effective area for adsorption, and to increase interaction force with guest molecules.

Herein, the additional material has at least one binding site for chemical bonding with the coordination polymer crystal, and thus can be grafted to the coordination polymer crystal, or can form a cross-linkage in the coordination polymer crystal. According to the grafting to the coordination polymer crystal and/or the forming a cross-linkage in the coordination polymer crystal, finally, the coordination polymer crystal according to the present invention has different properties of adsorbing or storing guest molecules.

Specifically, the additional material used for the present invention has at least one binding site for chemical bonding with the organic ligand and/or the metal, which forms the MOFs of the coordination polymer crystal. For example, when the additional material is an organic compound having at least one functional group such as a carboxyl group (—COOH) or an alcohol group (—OH), the organic compound can be covalently bonded to the organic ligand, or can be coordinated to the metal by the functional group functioning as a binding site. Also, when the additional material is a metal cluster formed by bonding between metal atoms, the metal cluster can be covalently bonded, coordinated, or chemically adsorbed to the organic ligand and/or the metal by the metal atoms functioning as binding sites. Also, when the additional material is an organometallic compound having at least one metal ion and functional group, the organometallic compound can be covalently bonded and/or coordinated to the organic ligand and/or the metal by the metal ion or the functional group functioning as a binding site.

Such an additional material can be grafted to the coordination polymer crystal, or can form a cross-linkage in the coordination polymer crystal, according to the number of binding sites chemically bonded to the coordination polymer crystal.

For example, in the case of an additional material having at least one binding site, when only one binding site is chemically bonded to any one site of the organic ligands and the metals of the coordination polymer crystal, the additional material can be grafted to the coordination polymer crystal. Also, in the case of an additional material having at least two binding sites, when the binding sites are chemically bonded to at least any two sites of the organic ligands and the metals of the coordination polymer crystal, the additional material can form a cross-linkage in the coordination polymer crystal.

Figure 4:
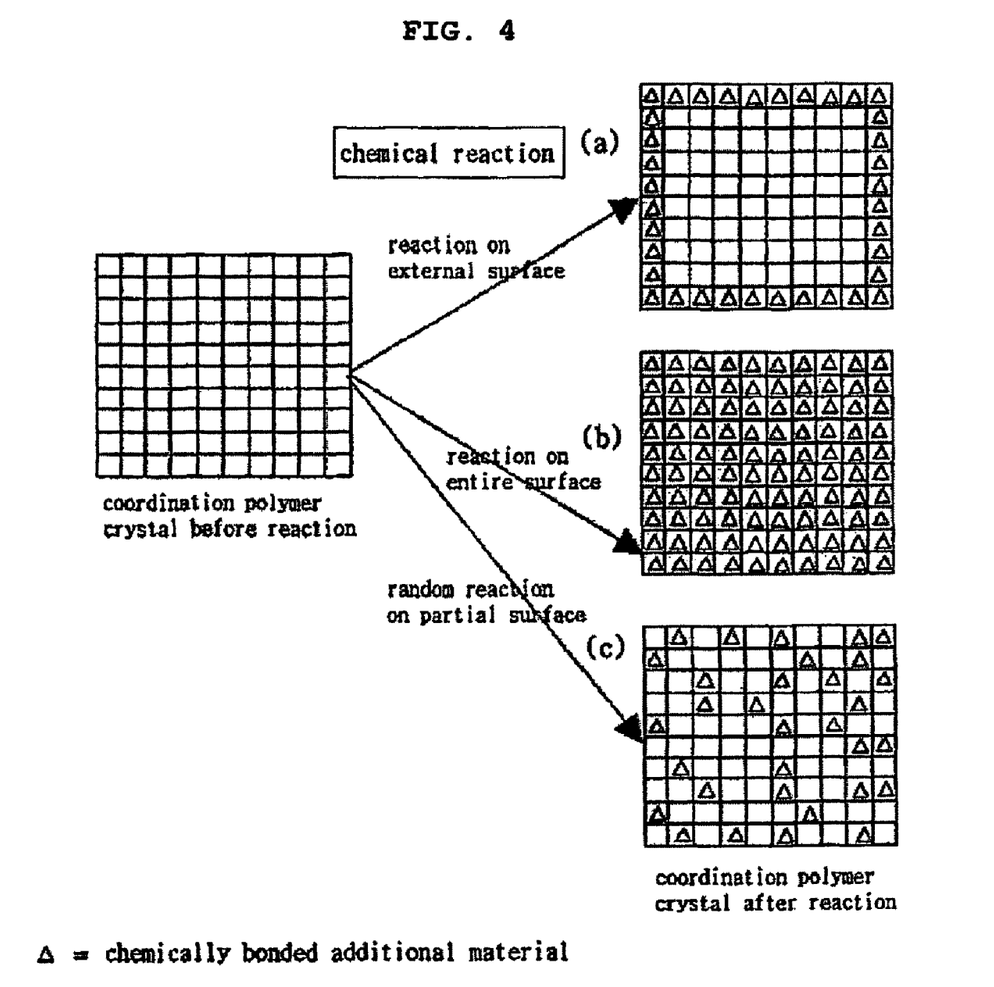
FIG. 4 is a schematic diagram illustrating a reaction of a coordination polymer crystal with porous MOFs with an additional material, and herein, (a) illustrates a reaction on the external surfaces, (b) illustrates a reaction on the entirety of the external surfaces and pore surfaces, and (c) illustrates a reaction on a portion of external surfaces and pore surfaces.

Herein, the position, where the additional material is grafted to the coordination polymer crystal or forms a cross-linkage in the coordination polymer crystal through a reaction, changes according to the size of the additional material. For example, if the size of the additional material is larger than or similar to the size of a pore within the coordination polymer crystal, it is not easy for the additional material to diffuse into the inside of the coordination polymer crystal. Then, chemical bonding of the additional material may be formed through a reaction on the outer surfaces of the coordination polymer crystal (see FIG. 4a). Also, if the size of the additional material is smaller than the size of a pore within the coordination polymer crystal, it is easy for the additional material to diffuse into the inside of the coordination polymer crystal. Then, chemical bonding of the additional material may be formed through a reaction on the surface of inside pores as well as on the outer surfaces of the coordination polymer crystal (see FIG. 4b).

In this manner, as the additional material is grafted or forms a cross-linkage on outer surfaces and/or pore surfaces of the coordination polymer crystal, finally, a coordination polymer crystal according to the present invention has different properties of adsorbing or storing guest molecules according to the additional material.

For example, when the additional material is grafted or forms a cross-linkage on a pore surface within the coordination polymer crystal, a pore size (average diameter) may be adjusted to be similar to a guest molecule (ex. hydrogen gas) size, that is, about 3-5 Å, due to the additional material. Accordingly, a final coordination polymer crystal according to the present invention can have small pores inside thereof. In addition, the bonded additional material can function as a new adsorption position for a guest molecule. Then, in the coordination polymer crystal according to the present invention, the distance of a guest molecule from a adsorption position may be within a range which van der Waals force can act, and thus it is possible to easily adsorb and store more guest molecules. Also, a metal cluster as an additional material has a stronger interaction force with a guest molecule than a adsorption position of the coordination polymer crystal for a guest molecule, and thus it is possible to increase the number of adsorbed guest molecules per unit area.

Figure 7:
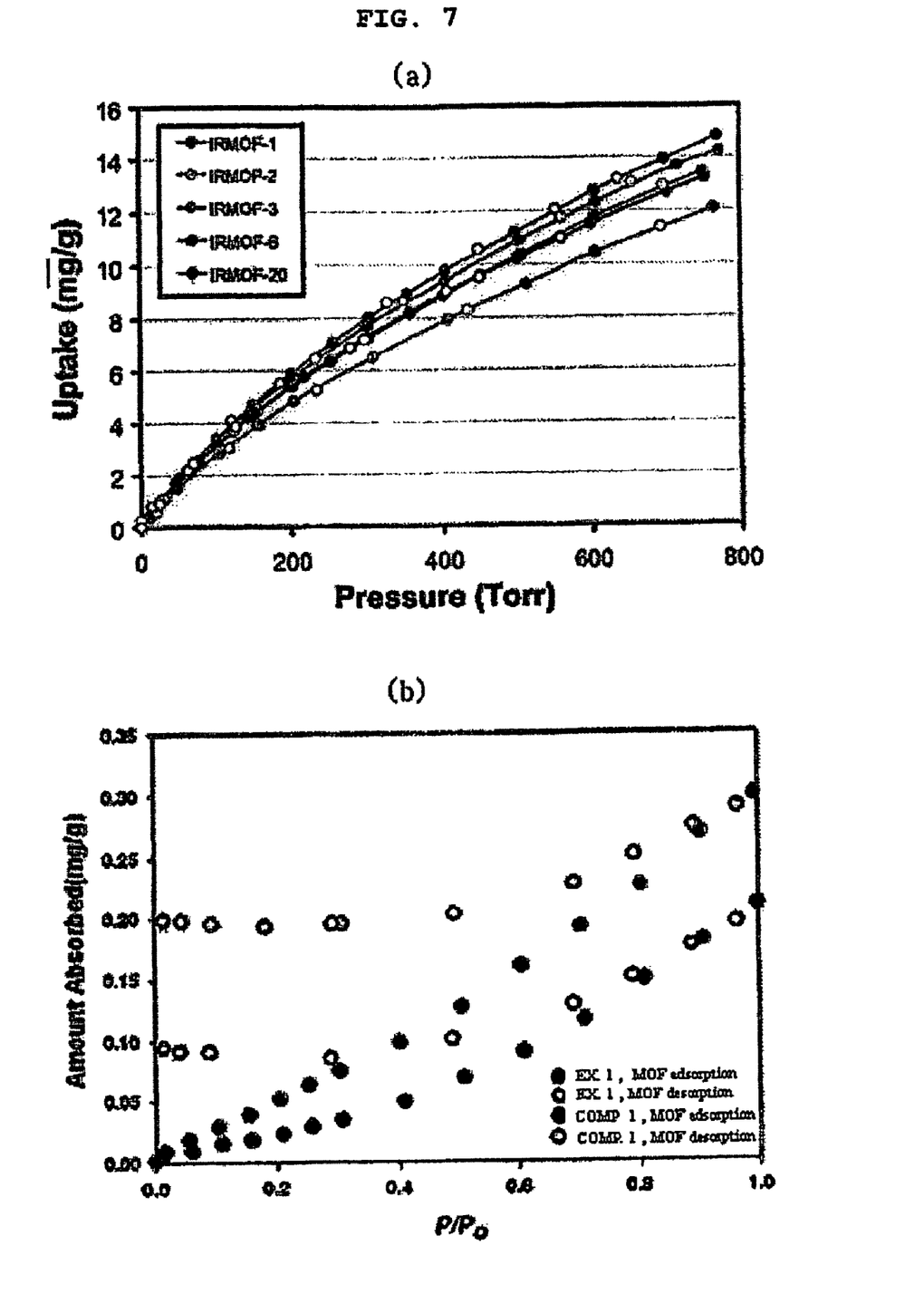
FIG. 7a is an $H_2$ adsorption isotherm of a coordination polymer crystal with porous MOFs according to comparative examples 1 to 5.
FIG. 7b is an $H_2$ adsorption isotherm of a coordination polymer crystal with porous MOFs according to examples 1 and 2. Herein, ● illustrates adsorption, and ○ illustrates desorption.

On the other hand, when the additional material is grafted onto outer surfaces of the coordination polymer crystal, the bonded additional material can function as a new adsorption position for a guest molecule, thereby allowing more guest molecules to be adsorbed and stored. Also, in this case, the grafted additional material exists on outer surfaces of the coordination polymer crystal, like a latch or a latching protrusion. Accordingly, even when a guest molecule adsorbed in the coordination polymer crystal is desorbed by a change in an ambient temperature or pressure, the guest molecule is not easily released due to the interference of the bonded additional material. Therefore, the coordination polymer crystal according to the present invention can store a guest molecule regardless of a change in an ambient temperature or pressure, and thus does not require expensive equipment for maintaining a fixed ambient temperature or pressure in storage or transport of a coordination polymer crystal. It seems that the coordination polymer crystal according to the present invention does not easily desorb an adsorbed guest molecule. This is contrary to a conventional coordination polymer crystal with porous MOFs, which reversibly adsorbs/desorbs a guest molecule (ex. Hydrogen gas) according to a change in a pressure (see FIG. 7a). In other words, it can be said that a coordination polymer crystal with porous MOFs according to the present invention irreversibly adsorbs/desorbs a guest molecule (see FIG. 7b).

Such a coordination polymer crystal with MOFs according to the present invention is represented by the following Formula 1.

$$[\{(M_aO_b)(L)_c\}\ldots(A)_m]_n \quad \text{[Formula 1]}$$

In formula 1, M is any one metal selected from the group consisting of group 3 to 16 metals, lanthanide metals and actinide metals of the Periodic Table, and alloys of at least two of these metals; L is selected from the group consisting of (however, there is no limitation); A is at least one kind of additional material selected from the group consisting of an organic compound, a metal cluster, and an organometallic compound; n indicates an integer between 1 and ∞ (preferably $8 \leq n \leq 10^{23}$); m indicates a random real number, $0 < m \leq 600$; a indicates a random real number, $0 < a \leq 100$; b indicates a random real number, $0 \leq b \leq 100$; and c indicates a random real number, $0 < c \leq 300$.

Herein, $[M_aO_b]$ indicates a metal portion forming the MOFs, and L portion, e.g.

indicates an organic ligand forming the MOFs. To such a metal and/or an organic ligand, an additional material, that is, (A)m, can be covalently bonded, coordinated, or chemically adsorbed. Especially, the additional material can be bonded to the organic ligand by a reaction of —NH$_2$ of the organic ligand with a binding site of the additional material, such as a functional group (ex. —Cl, —OH, etc.).

The coordination polymer crystal with MOFs according to the present invention includes a coordination polymer crystals represented by the following Formulas 2 and 3.

[Formula 2]

[Formula 3]

In formulas 2 and 3, n indicates an integer between 1 and ∞; and m indicates a random real number, $0 < m \leq 1$.

A coordination polymer crystal with porous MOFs that can be used in the present invention is formed by a coordinate bond of the metal and the organic ligand. Non-limited examples of the metal include group 3 to 16 metals, lanthanide metals and actinide metals of the Periodic Table, and alloys of at least two of these metals, but is not limited to that. Non-limited examples of the organic ligand include R—NH$_2$, R—OH, R—CHO, R—COX, R—COOH, R—NCY, R—N$_3$, R$^1$R$^2$C═CR$^3$R$^4$, and R$^1$—C≡C—R$^2$, etc. (each of R, R$^1$, R$^2$, R$^3$, and R$^4$ independently has C1~C50, and is selected from the group consisting of substituted/unsubstituted aromatic compounds, aliphatic compounds, and heterocyclic compounds; X includes an element of group 17 of the Periodic Table; and Y includes an element of group 16 of the Periodic Table), but is not limited to that. Herein, the organic ligand can easily react with a functional group represented by the following table 1.

TABLE 1

| Organic Ligand | Functional Groups |
|---|---|
| R—NH$_2$ | —COOH, —COX, —CO—O—OC—, —NCY, —CHO, —OCOX, —SO$_2$X, —X |
| R—OH | —COOH, —COX, —CO—O—OC—, —OH, —OCOX, —NCY |
| R—CHO | —NH$_2$, —ONH$_2$, $\overset{\mid}{-\text{N}}-\text{NH}_2$ |
| R—COX | —OH, —NH$_2$ |
| R—COOH | —NH—, —O— |
| R—NCY | —NH—, —OH |
| R—N$_3$ | —C≡C— |
| R—C≡C— | —N$_3$ |

X indicates an element of group 17 of the Periodic Table; and Y indicates an element of group 16 of the Periodic Table. However, there is no limitation.

An additional material that can be used in the present invention includes an organic compound, a metal cluster, and an organometallic compound, etc. Also, such an additional material can be used alone, or can be used by mixing at least two of these materials.

There is no limitation in using an organic compound in the present invention, as long as the organic compound contains a functional group as known to those skilled in the art, such as functional groups shown in Table 1. Specifically, examples of the organic compound include R—COOH, R—COX, R$^1$—CO—O—OC—R$^2$, R—NCY, R—CHO, R—O—COX, R—SO$_2$X, R—X, R—OH, R—NH$_2$, R—ONH$_2$, R$^1$—NR$^2$H$_2$, R$^1$—NH—R$^2$, R$^1$—O—R$^2$, R$^1$R$^2$—C═R$^3$R$^4$, R$^1$—C≡C—R$^2$, and R—N$_3$, etc. Herein, each of R, R$^1$, R$^2$, R$^3$, and R$^4$ independently has C1~C50, and is selected from the group consisting of substituted/unsubstituted aromatic compounds, aliphatic compounds, and heterocyclic compounds; X includes an element of group 17 of the Periodic Table; and Y includes an element of group 16 of the Periodic Table.

Also, there is no limitation in using a metal cluster in the present invention, as long as the metal cluster is a compound formed by bonding between metal atoms. Specifically, examples of the metal atom include group 1 to 16 metal atoms of the Periodic Table. More specifically, examples of the metal atom include, but are not limited to: Li, Na, Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Al, Ga, In, Tl, Si, Ge, Sn, Pb, As, Sb, Bi, etc. Herein, it is preferable that the number of metal atoms forming the metal cluster is about 1~400, but is not limited to that.

Also, there is no limitation in using an organometallic compound in the present invention, as long as the organic compound contains a metal ion and a functional group as known to those skilled in the art, such as metal ions and functional groups shown in Table 1. Specifically, non-limited examples of the functional group of the organometallic compound include —COOH, —COX, —CO—O—OC—, —NCY, —CHO, —SO$_2$X, —X, —OCOX, —NH$_2$, —ONH$_2$, —NH—, —O—, —C≡C—, and —N$_3$, etc. (herein, X includes an element of group 17 of the Periodic Table; and Y includes an element of group 16 of the Periodic Table). Also, non-limited examples of the metal ion of the organometallic compound include group 1 to 16 metal ions of the Periodic Table, and more specifically, include, but are not limited to: Li$^+$, Na$^+$, Mg$^{2+}$, Ca$^{2+}$, Sr$^{2+}$, Ba$^{2+}$, Sc$^{3+}$, Y$^{3+}$, Ti$^{4+}$, Zr$_{4+}$, Hf$^{4+}$, V$^{4+}$, V$^{3+}$, V$^{2+}$, Nb$^{3+}$, Ta$^{3+}$, Cr$^{3+}$, Mo$^{3+}$, W$^{3+}$, Mn$^{3+}$, Mn$^{2+}$, Re$^{3+}$, Re$^{2+}$, Fe$^{3+}$, Fe$^{2+}$, Ru$^{3+}$, Ru$^{2+}$, Os$^{3+}$, Os$^{2+}$, Co$^{3+}$, Co$^{2+}$, Rh$^{2+}$, Rh$^+$, Ir$^{3+}$, Ir$^{2+}$, Ir$^+$, Ni$^{2+}$, Ni$^+$, Pd$^{2+}$, Pd$^+$, Pt$^{2+}$, Pt$^+$, Cu$^{2+}$, Cu$^+$, Ag$^+$, Au$^+$, Zn$^{2+}$, Cd$^{2+}$, Hg$^{2+}$, Al$^{3+}$, Ga$^{3+}$, In$^{3+}$, Tl$^{3+}$, Si$^{4+}$, Si$^{2+}$, Ge$^{4+}$, Ge$^{2+}$, Sn$^{4+}$, Sn$^{2+}$, Pb$^{4+}$, Pb$^{2+}$, As$^{5+}$, As$^{3+}$, As$^+$, Sb$^{5+}$, Sb$^{3+}$, Sb$^+$, Bi$^{5+}$, Bi$^{3+}$, Bi$^+$, etc.

A method of preparing a coordination polymer crystal with MOFs according to the present invention includes the steps of, but is not limited to: (i) preparing a coordination polymer crystal with porous MOFs; and (ii) chemically bonding at least one kind of additional material selected from the group consisting of an organic compound, a metal cluster, and an organometallic compound, to the coordination polymer crystal.

In step (ii), it is preferable that additional material content is about $10^{-23}$~1 times as many as the number of binding sites within the crystal, which can be chemically bonded with the additional material.

Step (ii) may be performed in a solvent, and includes the steps of: soaking the coordination polymer crystal with porous MOFs in the solvent; and adding at least one kind of additional material with the solution, and reacting the additional material with the coordination polymer crystal with porous MOFs.

Herein, there is no limitation in using a solvent in the present invention, as long as the solvent is generally used by those skilled in the art. Examples of the solvent include, but are not limited to: water, methanol, ethanol, propanol, isopropanol, butanol, pentanol, hexanol, dimethyl sulphoxide (DMSO), N,N-dimethylformamide (DMF), ethylene glycol, ethylene glycol monomethyl ether, ethylene glycol dimethyl ether, propylene glycol, propylene glycol propyl ether, propylene glycol methyl ether acetate, N-methyl pyrrolidone, methyl isobutyl ketone, methyl ethyl ketone, acetonitrile, tetrahydrofuran (THF), hexadecane, pentadecane, tetradecane, tridecane, dodecane, undecane, decane, nonane, octane, heptane, hexane, xylene, toluene, benzene, 2,6-lutidine, dichloromethane, etc. Also, such a solvent can be used alone, or can be used by mixing at least two of these materials. Especially, it is preferable that 2,6-lutidine or dichloromethane is used.

Besides, in step (ii), the additional material is heated at a temperature of about 110~600° C., preferably about 200~500° C., and thus may be chemically bonded to the crystal as a gas phase.

As described above, the coordination polymer crystal with MOFs according to the present invention can selectively adsorb or store different materials regardless of an ambient temperature or pressure. Accordingly, the coordination polymer crystal with MOFs according to the present invention can be used for adsorbents, catalysts, catalyst carriers, sensors, fluid adsorbents/separators, desiccants, ion exchange materials, molecular sieves (separator), materials for chromatography, selective release and absorption of a molecule, molecular recognition, nanotubes, nano reactors, etc. Especially, the coordination polymer crystal according to the present invention can adsorb or store various materials such as water, ammonia, carbon dioxide, carbon monoxide, hydrogen, amine, methane, oxygen, argon, nitrogen, etc.

Hereinafter, examples and comparative examples according to the present invention will be described. However; the following examples and comparative examples do not limit the idea of the present invention.

EXAMPLE 1

Figure 2:
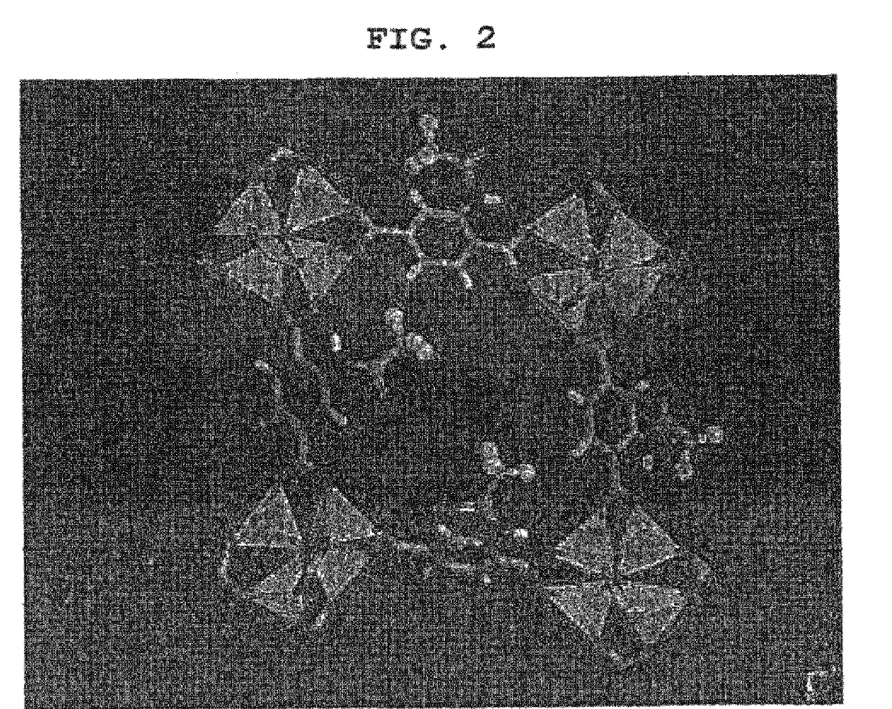
FIG. 2 is a three-dimensional structural view illustrating one side of a lattice cell in a coordination polymer crystal with porous MOFs according to example 1 of the present invention.

1 g of IRMOF-3 [$Zn_4O(C_8H_5NO_4)$] crystal was added to 100 ml of dichloromethane (solvent, Aldrich) to prepare a solution. 15 equivalent weight of acetyl chloride (based on 1 equivalent weight of amine group of IRMOF-3) and 15 equivalent weight of 2,6-lutidine were added to the solution; and were prepared into a mixed solution through agitation for 24 hours at a room temperature. Then, the mixed solution was filtered, and a crystal was formed. The crystal was cleaned by dichloromethane, was dried in a vacuum, and was finally prepared into a coordination polymer crystal with metal-organic frameworks (MOFs). The finally prepared coordination polymer crystal can be represented by formula 2, and has a three-dimensional structure as shown in FIG. 2.

EXAMPLE 2

Figure 3:
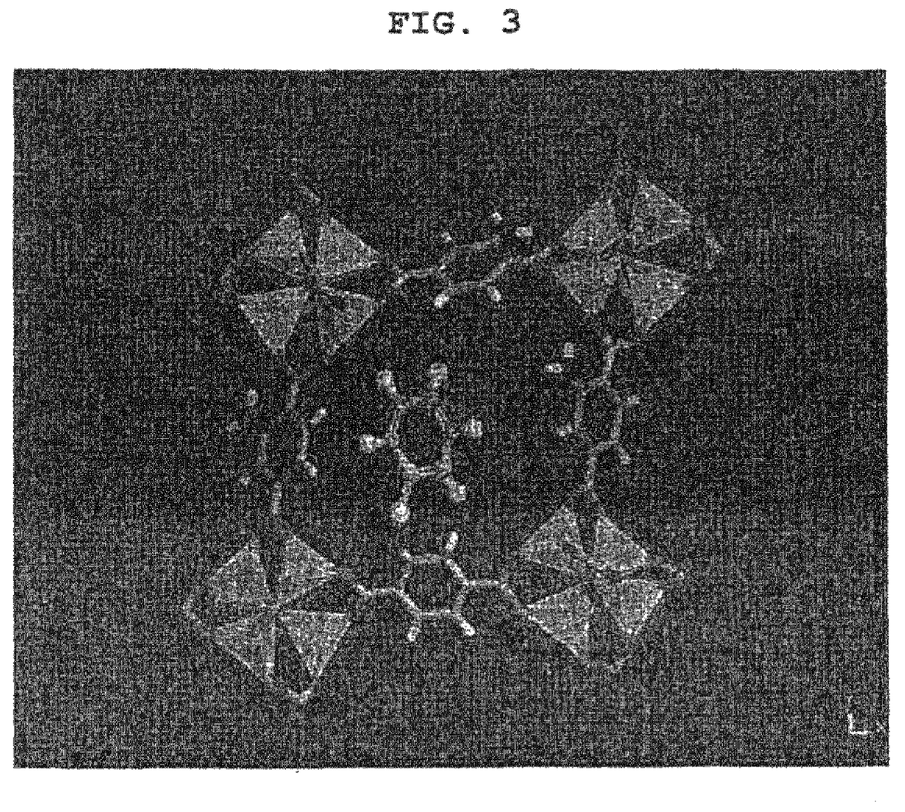
FIG. 3 is a three-dimensional structural view illustrating one side of a lattice cell in a coordination polymer crystal with porous MOFs according to example 2 of the present invention.

A coordination polymer crystal with MOFs was prepared in the same manner as described in example 1, except that instead of 15 equivalent weight of acetyl chloride, 30 equivalent weight of benzaldehyde was used. The finally prepared coordination polymer crystal can be represented by formula 3, and has a three-dimensional structure as shown in FIG. 3.

COMPARATIVE EXAMPLES 1~5

IRMOF-1 [$Zn_4O(C_8H_4O_4)_3$], IRMOF-2 [$Zn_4O(C_8H_3BrO_4)_3$], IRMOF-3 [$Zn_4O(C_8H_5NO_4)_3$], IRMOF-6 [$Zn_4O(C_{10}H_6O_4)_3$], and IRMOF-20 [$Zn_4O(C_8H_2O_4S_2)_3$] as known to those skilled in the art were used.

EXAMPLE 1

Chemical Structure

Figure 5:
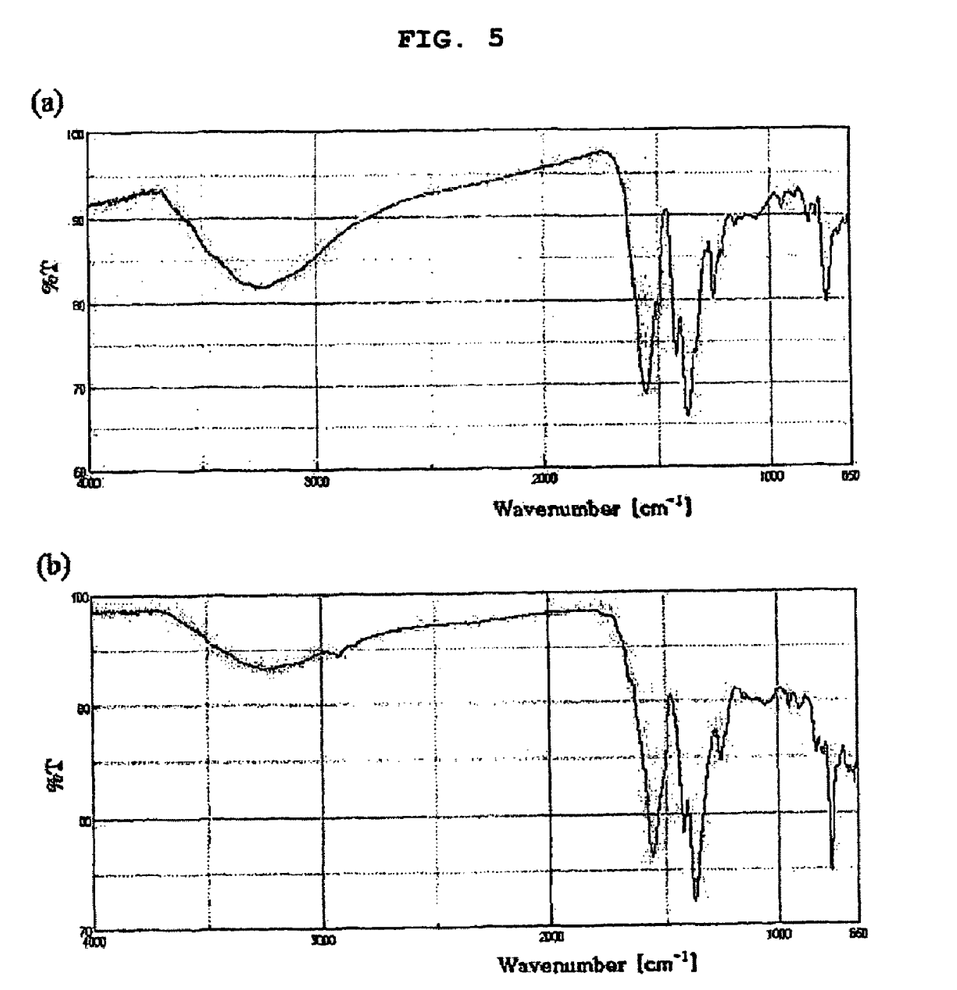
FIG. 5a is a graph illustrating an Infrared(IR) spectrum of a conventional coordination polymer crystal (IRMOF-3) with porous MOFs according to comparative example 3.
FIG. 5b is a graph illustrating an IR spectrum of a coordination polymer crystal with porous MOFs according to example 1 of the present invention.

In order to determine the chemical structure of the coordination polymer crystal with MOFs prepared in example 1, infrared Spectroscopy (IR) was used to analyze a spectrum of a test sample. Herein, as a control group, an IR spectrum of $IRMOF_3$ (comparative example 3) was measured. The measurement results are shown in the FIG. 5.

FIG. 5a illustrates the IR spectrum of IRMOF-3 (comparative example 3) as a control group. The graph shows peaks at 3240(br), 1560(s, nas COO⁻), 1495(m), 1420(m), 1370(s, ns COO⁻), 1250(m), 1155(w), 945(w), 890(w), 830(w), 795(w), 753(m), 700(w), and 660(w).

On the other hand, FIG. 5b illustrates an IR spectrum of the coordination polymer crystal with MOFs prepared in example 1. Herein, the graph shows peaks at 3240(br), 2925 (w), 2855(w), 1654(w, amide), 1560(s, nas COO⁻), 1495(sh), 1420(m), 1370(s, ns COO⁻), 1250(m), 1155(w), 945(w), 900 (w), 830(w), 795(w), 767(m), 690(w), and 665(w) cm⁻¹. The peaks of this graph occur at a very similar wavelength to the control group IRMOF-3. Accordingly, it was found that the coordination polymer crystal with MOFs prepared in example 1 has a very similar chemical structure to the control group IRMOF-3.

However, contrary to the IR spectrum of the control group IRMOF-3, the IR spectrum of the coordination polymer crystal with MOFs prepared in example 1 shows a peak at about 1654 cm⁻¹, which is a distinct peak only when there exists an amide group (—NHCO—). Therefore, it was found that in the coordination polymer crystal with MOFs according to the present invention, acetyl chloride was bonded to IRMOF-3.

EXAMPLE 2

Crystal Structure

In order to analyze a crystal structure of the coordination polymer crystal with MOFs prepared in example 1, X-ray powder diffraction (XRPD) was used to analyze an XRPD pattern of a test sample. Herein, an XRPD pattern of IRMOF-3 (comparative example 3) as a control group was analyzed. The analysis results are shown in the FIG. 6.

Figure 6:
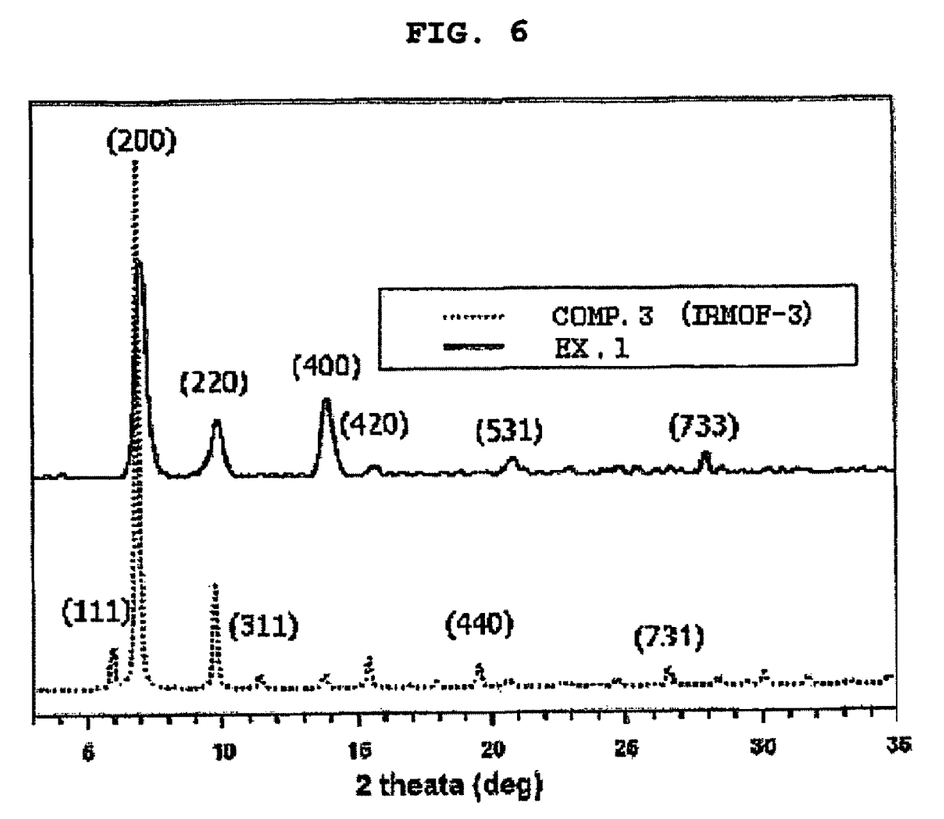
FIG. 6 is a graph illustrating an XRPD (X-ray powder diffraction) pattern of a coordination polymer crystal with porous MOFs according to example 1 and comparative example 3.

FIG. 6 shows a distinct peak describing that both of the coordination polymer crystal with MOFs prepared in example 1, and IRMOF-3 are crystalline. Also, it was found that the coordination polymer crystal with MOFs prepared in example 1 has a very similar XRPD pattern to IRMOF-3. Herein, some parts of the pattern, which are different from the IRMOF-3 pattern, seem to be caused by acetyl chloride bonded to IRMOF-3.

Therefore, it was found that the coordination polymer crystal with MOFs according to the present invention has a crystal structure, like a conventional coordination polymer crystal with MOFs.

EXAMPLE 3

Adsorption/Desorption Properties of the Coordination Polymer Crystal with MOFs In order to determine the adsorption/desorption properties of the coordination polymer crystal with MOFs according to the present invention, the following analysis was performed.

In this analysis, the coordination polymer crystal with MOFs prepared in examples 1 and 2 was used. Also, as a control group, IRMOF-1, IRMOF-2, IRMOF-3, IRMOF-6, and IRMOF-20 prepared in comparative examples 1-5 were used. Hydrogen gas ($H_2$) was adsorbed to each test sample by increasing pressure to 1 atm, at a temperature of 77 K, and then was desorbed from the test sample by decreasing pressure. The experimental results are shown in the FIG. 7.

According to the experimental results, as shown in FIG. 7a, in the coordination polymer crystals with MOFs prepared in comparative examples 1~5, the adsorption and desorption paths of hydrogen gas are very similar to each other. In other words, the coordination polymer crystals with MOFs prepared in comparative examples 1~5 reversibly adsorbed and desorbed hydrogen gas.

On the other hand, as shown in FIG. 7b, in the coordination polymer crystals with MOFs prepared in examples 1 and 2, the adsorption and desorption paths of hydrogen gas are not similar to each other. In other words, in the coordination polymer crystals with MOFs prepared in examples 1 and 2, there was an irreversible hysteresis phenomenon.

The hysteresis phenomenon occurs because even when adsorbed hydrogen gas is desorbed by a change in an ambient temperature, the desorbed hydrogen gas cannot be easily released due to the interference of an additional material existing in the coordination polymer crystal with MOFs according to the present invention.

INDUSTRIAL APPLICABILITY

In a coordination polymer crystal with porous MOFs according to the present invention, an additional material such as an organic compound, a metal cluster, and an organometallic compound is chemically bonded to the coordination polymer crystal itself, thereby allowing more guest molecules to be easily adsorbed and stored regardless of a change in an ambient temperature or pressure.

While this invention has been described in connection with what is presently considered to be the most practical and exemplary embodiment, it is to be understood that the invention is not limited to the disclosed embodiment and the drawings, but, on the contrary, it is intended to cover various modifications and variations within the spirit and scope of the appended claims.

The invention claimed is:

1. A coordination polymer crystal with porous metal-organic frameworks, the polymer crystal comprising a metal and an organic ligand in which the metal is coordinated to the organic ligand,
wherein, while a crystal state of the coordination polymer crystal is maintained, at least one additional material selected from the group consisting of an organic compound, a metal cluster, and an organometallic compound is chemically bonded to the organic ligand and/or the metal of the coordination polymer crystal.

2. The coordination polymer crystal as claimed in claim 1, wherein the chemical bond is a covalent bond, a coordinate bond, or chemical adsorption.

3. The coordination polymer crystal as claimed in claim 1, wherein the additional material has at least one binding site for chemical bonding with the coordination polymer crystal, and is grafted to the coordination polymer crystal when only one binding site of the additional material is chemically bonded to the coordination polymer crystal.

4. The coordination polymer crystal as claimed in claim 1, wherein the additional material has at least two binding sites for chemical bonding with the coordination polymer crystal, and forms a cross-linkage in the coordination polymer crystal when the binding sites of the additional material are chemically bonded to the coordination polymer crystal.

5. The coordination polymer crystal as claimed in claim 1, wherein an average diameter of a pore is adjusted within a range of 3-5 Å by the additional material.

6. The coordination polymer crystal as claimed in claim 1, wherein the organic compound as the additional material is selected from the group consisting of R—COOH, R—COX, $R^1$—CO—O—OC—$R^2$, R—NCY, R—CHO, R—O—COX, R—$SO_2$X, R—X, R—OH, R—$NH_2$, R—$ONH_2$, $R^1$—$NR^2NH_2$, $R^1$—NH—$R^2$, $R^1$—O—$R^2$, $R^1R^2$C=$R^3R^4$, $R^1$—C≡C—$R^2$, and R—$N_3$ (wherein each of R, $R^1$, $R^2$, $R^3$, and $R^4$ independently has C1-C50, and is selected from the group consisting of substituted/unsubstituted aromatic compounds, aliphatic compounds, and heterocyclic compounds; X comprises an element of group 17 of the Periodic Table; and Y comprises an element of group 16 of the Periodic Table).

7. The coordination polymer crystal as claimed in claim 1, wherein the metal cluster as the additional material is a compound formed by bonding between metal atoms selected from the group consisting of group 1 to 16 metals of the Periodic Table.

8. The coordination polymer crystal as claimed in claim 7, wherein the metal atoms of the metal cluster are selected from the group consisting of Li, Na, Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Al, Ga, In, Tl, Si, Ge, Sn, Pb, As, Sb, and Bi.

9. The coordination polymer crystal as claimed in claim 1, wherein the organometallic compound as the additional material contains a metal ion and organic ligands with functional groups.

10. The coordination polymer crystal as claimed in claim 9, wherein the metal ion of the organometallic compound is selected from the group consisting of $Li^+$, $Na^+$, $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3-}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{3+}$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^+$, $Sb^{5+}$, $Sb^{3+}$, $Sb^+$, $Bi^{5+}$, $Bi^{3+}$, and $Bi^+$.

11. The coordination polymer crystal as claimed in claim 9, wherein the functional group of the organometallic compound is selected from the group consisting of —COOH, —COX, —CO—O—OC—, —NCY, —CHO, —$SO_2$X, —X, —OH, —OCOX, —$NH_2$, —$ONH_2$, —NH—, —O—, —C≡C—, and —$N_3$ (herein, X comprises an element of group 17 of the Periodic Table; and Y comprises an element of group 16 of the Periodic Table).

12. The coordination polymer crystal as claimed in claim 1, wherein an organic ligand forming MOFs in the coordination polymer crystal is selected from the group consisting of R—$NH_2$, R—OH, R—CHO, R—COX, R—COOH, R—NCY, R—$N_3$, $R^1R^2$C=$CR^3R^4$, and R1-C≡C—$R^2$ (wherein each of R, $R^1$, $R^2$, $R^3$, and $R^4$ independently has C1-C50, and is selected from the group including substituted/unsubstituted aromatic compounds, aliphatic compounds, and heterocyclic compounds; X comprises an element of group 17 of the Periodic Table; and Y comprises an element of group 16 of the Periodic Table).

13. The coordination polymer crystal as claimed in claim 1, wherein a metal forming MOFs in the coordination polymer crystal is selected from the group consisting of group 3 to 16 metals, lanthanide metals and actinide metals of the Periodic Table, and alloys of at least two of these metals.

14. The coordination polymer crystal as claimed in claim 1, which is represented by the following Formula 1:

$$[\{(M_aO_b)(L)_c\}\ldots(A)_m]_n \qquad \text{(Formula 1)}$$

(in formula 1, M is any one metal selected from the group consisting of group 3 to 16 metals, lanthanide metals and actinide metals of the Periodic Table, and alloys of at least two of these metals; L is selected from the group consisting of A is at least one kind of additional material selected from the group consisting of an organic compound, a metal cluster, and an organometallic compound; n indicates an integer between 1 and ∞; m indicates a random real number, $0 < m \leq 600$; a indicates a random real number, $0 < a \leq 100$; b indicates a random real number, $0 \leq b \leq 100$; c indicates a random real number, and $0 < c \leq 300$).

15. The coordination polymer crystal as claimed in claim 1, which is used for adsorbents, molecular sieves, catalysts, catalyst carriers, sensors, desiccants, ion exchange materials, fluid adsorbents/separators, materials for chromatography, selective release and absorption of a molecule, molecular recognition, nanotubes, or nano reactors.

16. The coordination polymer crystal as claimed in claim 1, which can adsorb or store water, ammonia, carbon dioxide, carbon monoxide, hydrogen, amine, methane, oxygen, argon, or nitrogen.

17. A method of preparing a coordination polymer crystal as claimed in claim 1, the method comprising the steps of:
  (i) preparing a coordination polymer crystal with porous metal-organic frameworks, the polymer crystal comprising a metal and an organic ligand in which the metal is coordinated to the organic ligand; and
  (ii) chemically bonding at least one additional material selected from the group consisting of an organic compound, a metal cluster, and an organometallic compound, to the metal or the organic ligand of the coordination polymer crystal.

18. The method as claimed in claim 17, wherein in step (ii), content of the additional material is about $10^{-23}$-1 times as many as a number of binding sites within the coordination polymer crystal, which can be chemically bonded with the additional material.

19. The method as claimed in claim 17, wherein step (ii) is performed in a solvent, and the solvent is selected from the group consisting of 2,6-lutidine, dichloromethane, and a mixture thereof.

20. The method as claimed in claim 17, wherein in step (ii), the additional material is heated at a temperature of 110-600° C., and thus is chemically bonded to the coordination polymer crystal as a gas phase.

* * * * *